(12) United States Patent
Greene (10) Patent No.: US 9,107,579 B2
(45) Date of Patent: Aug. 18, 2015

(54) SYSTEMS, METHODS AND APPARATUS FOR POWERING DEVICES USING RF ENERGY FROM A MOBILE TRANSMITTER

(75) Inventor: Charles E. Greene, Cabot, PA (US)

(73) Assignee: Powercast Corporation, Pittsburgh, PA (US)

(*) Notice: Subject to any disclaimer, the term of this patent is extended or adjusted under 35 U.S.C. 154(b) by 653 days.

(21) Appl. No.: 13/324,730

(22) Filed: Dec. 13, 2011

(65) Prior Publication Data

US 2012/0316414 A1    Dec. 13, 2012

Related U.S. Application Data (60) Provisional application No. 61/422,829, filed on Dec. 14, 2010.

(51) Int. Cl.
| | |
|---|---|
| *H04W 88/06* | (2009.01) |
| *A61B 5/00* | (2006.01) |
| *H02J 7/02* | (2006.01) |
| *H04W 4/00* | (2009.01) |

(52) U.S. Cl.
CPC ............... *A61B 5/0024* (2013.01); *H02J 7/025* (2013.01); *A61B 2560/0214* (2013.01); *A61B 2560/0219* (2013.01); *A61B 2560/045* (2013.01); *H04W 4/008* (2013.01); *H04W 88/06* (2013.01)

(58) Field of Classification Search
USPC .......................... 455/78, 562.1, 571, 573, 574
See application file for complete search history.

(56) References Cited

U.S. PATENT DOCUMENTS

2008/0301292 A1* 12/2008 Oya ............................... 709/224

* cited by examiner

*Primary Examiner* — Sam Bhattacharya
(74) *Attorney, Agent, or Firm* — Cooley LLP (57) ABSTRACT

In some embodiments, a personal area network (PAN) includes a mobile transmitter (e.g., a mobile or cellular phone) and one or more devices (e.g., sensors) that require power to operate (e.g., collect data). The mobile transmitter can be configured to transmit a sufficient amount of power (e.g., RF energy) to the one or more devices to power the one or more local devices. In addition to transmitting power, the mobile transmitter can be configured to communicate over a wireless network (e.g., a cellular network) as its primary function.

26 Claims, 4 Drawing Sheets

SYSTEMS, METHODS AND APPARATUS FOR POWERING DEVICES USING RF ENERGY FROM A MOBILE TRANSMITTER

CROSS REFERENCE TO RELATED APPLICATION

This application claims priority to and the benefit of U.S. Provisional Application No. 61/422,829, entitled "Systems, Methods and Apparatus for Powering Devices Using RF Energy from a Mobile Transmitter," filed Dec. 14, 2010; the disclosure of which is incorporated by reference herein in its entirety.

BACKGROUND

Systems, methods and apparatus for wirelessly powering devices are described, including, for example, systems, methods and apparatus for wirelessly powering devices using radio frequency (RF) energy from a mobile transmitter.

Currently, a growing number of electronic devices are designed and manufactured for use in a personal area network (PAN). For example, many known devices are designed for use within ten meters (or approximately 33 feet) of a person and are usually untethered (or wireless). One option for powering these PAN devices is by use of a battery. These batteries, however, are recharged to provide continuous, long-term use.

Mobile devices, such as cellular phones, are increasingly becoming smart and capable of operating in a multitude of functions or modes. These mobile devices, however, are typically only being used to performancillary functions or operations, such as running software applications. The capabilities of these mobile devices are typically being underused.

Thus, a need exists for a system, method and apparatus for recharging the batteries of PAN devices or eliminating the batteries in PAN devices altogether. In both instances, RF energy can be used to provide power to PAN devices.

SUMMARY

Systems, methods and apparatus for wirelessly powering devices using radio frequency (RF) energy are described herein. In some embodiments, a personal area network (PAN) includes a mobile transmitter (e.g., a mobile or cellular phone) and one or more devices (e.g., sensors) that use power to operate (e.g., collect data). The mobile transmitter can be configured to transmit a sufficient amount of power (e.g., RF energy) to the one or more devices to power the one or more local devices. In addition to transmitting power, the mobile transmitter can be configured to communicate over a wireless network (e.g., a cellular network) as its primary function.

DETAILED DESCRIPTION

Systems, methods and apparatus for wirelessly powering devices using radio frequency (RF) energy are described herein. In some embodiments, a personal area network (PAN) includes a mobile transmitter (e.g., a mobile or cellular phone) and one or more devices (e.g., sensors) that use power to operate (e.g., collect data). The mobile transmitter can be configured to transmit a sufficient amount of power (e.g., RF energy) to the one or more devices to power the one or more local devices. In addition to transmitting power, the mobile transmitter can be configured to communicate over a wireless network (e.g., a cellular network) as its primary function.

Figure 1:
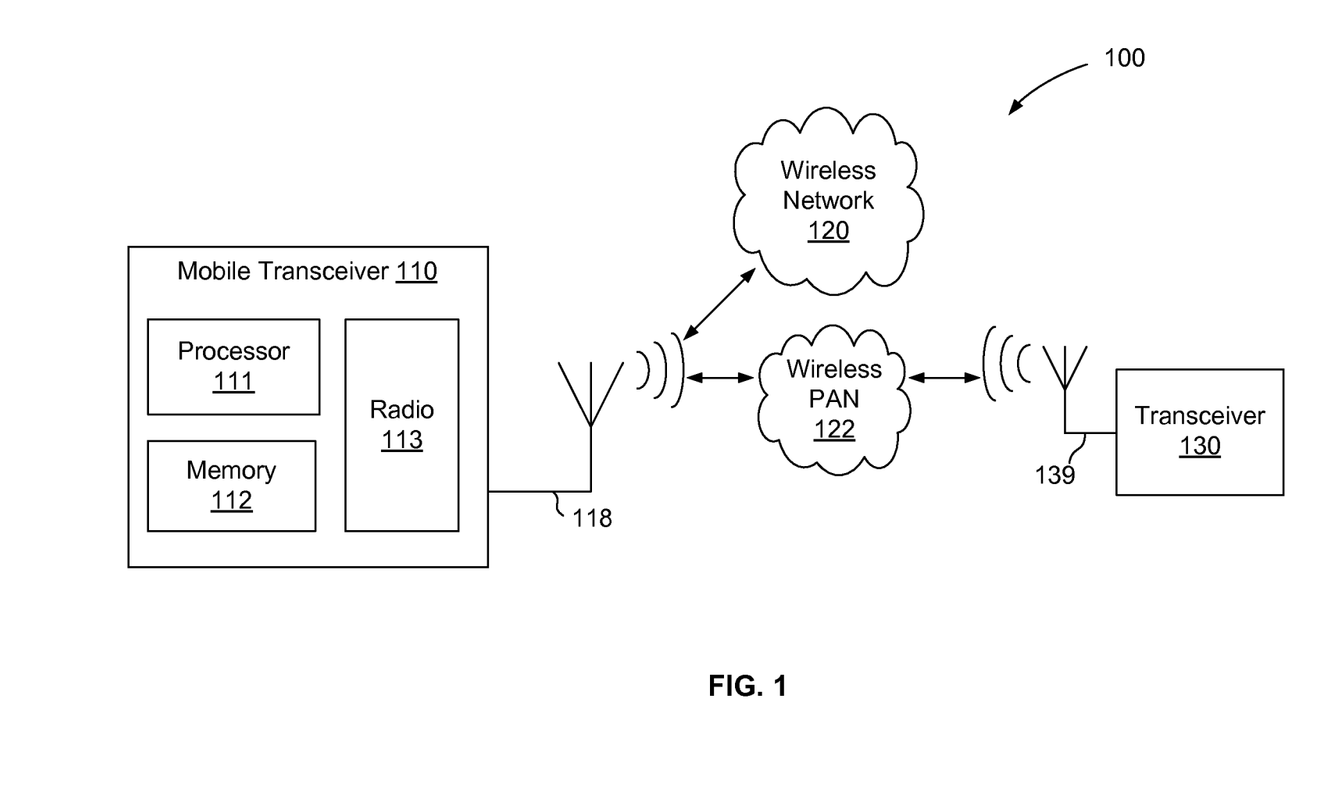
FIG. 1 is a schematic illustration of a wireless powering system according to an embodiment.

FIG. 1 is a schematic illustration of a wireless powering system 100 for powering devices in a wireless personal area network (PAN). The system 100 includes a mobile transceiver 110, a transceiver 130, a wireless network 120 and a wireless PAN 122. The mobile transceiver 110 and the transceiver 130 are located within the operational range of the wireless PAN 122 and are configured to communicate with each other via the wireless PAN 122, as discussed in more detail herein. The mobile transceiver 110 is also configured to send power to the transceiver 130 via the wireless PAN 122, as discussed in more detail herein. In some embodiments, the mobile transceiver 110 is configured to communicate with other devices and/or structures (not illustrated) via the wireless network 120, as discussed in more detail herein. The mobile transceiver 110 can be any suitable mobile device, such as, for example, a mobile phone, a cellular phone, a smartphone, a personal data assistant (PDA) and/or any other mobile device capable of communicating with other devices over the wireless PAN 122 or the wireless network 120. The wireless network 120 can be any suitable wireless network, such as, for example, a wireless local area network (LAN), a wireless wide area network (WAN), a WiMAX, a cellular network, and/or the like.

The mobile transceiver 110 includes a processor 111, a memory 112, a radio 113 and an antenna 118 (collectively, "components"). Each of the components of the mobile transceiver 110 can be interconnected and/or configured to communicate with one another, either directly or indirectly. The processor 111 can be configured to control the operation of the mobile transceiver 110, including controlling the operation of the memory 112, the radio 113, and/or the antenna 118. The processor 111 can be, for example, a microprocessor, a field programmable gate array (FPGA) and/or the like. In some embodiments, the processor 111 is configured to operate or function in a manner similar to a processor of a smartphone. The memory 112 can be, for example, a storage device such as Random Access Memory (RAM), Read Only Memory (ROM), etc. In some embodiments, the memory 112 is configured to operate, function and/or store data in a manner similar to a memory of a smartphone. The radio 113 is configured to generate a signal (e.g., a radio frequency (RF) signal) to be wirelessly transmitted by the antenna 118 over the wireless network 120 or the wireless PAN 122. The signal can be, for example, a data signal, a data signal with a power component, a power signal, and/or the like. The radio 113 can be any suitable radio, such as, for example, a transmitter or transceiver operating at any appropriate frequency band (e.g. RF band, Cellular band, ISM band, Licensed band, Unlicensed band).

The antenna 118 of the mobile transceiver 110 is configured to wirelessly transmit and receive signals via the wireless network 120 and/or the wireless PAN 122. For example, the antenna 118 can receive a power signal from the radio 113 and then transmit that power signal to the transceiver 130 through the wireless PAN 122. In embodiments where the mobile transceiver 110 is a smartphone, the antenna 118 can wirelessly receive a signal from a cell tower located within the range of the wireless network 120. In this manner, the mobile transceiver 110 can transmit and/or receive calls and/or data (e.g., emails) via the wireless network 120 using the antenna 118. The antenna 118 can be any suitable antenna such as a dipole antenna, a monopole antenna, a patch antenna, multi-band antenna, and/or the like. Although the antenna 118 is illustrated in FIG. 1 as being external to the mobile transceiver 110, in other embodiments, the antenna 118 (or at least a portion of the antenna 118) is located within mobile transceiver 110.

The transceiver 130 is configured to wirelessly transmit and/or receive signals over the wireless PAN 122 via an antenna 139. For example, the antenna 139 of the transceiver 130 can wirelessly receive power (e.g., pulsed RF energy, continuous RF energy, intermittent RF energy, multi-band RF energy) transmitted from the antenna 118 of the mobile transceiver 110 via the wireless PAN 122. In some embodiments, the transceiver 130 is configured to convert the received power into a current (e.g., a direct current) and use that current to power the transceiver 130 during operation. In some embodiments, the transceiver 130 includes a charge storage component (e.g., a battery, a supercapacitor, an energy cell) configured to store at least a portion of the current so that the current can be used at a later time to power the transceiver 130. In some embodiments, the transceiver 130 is configured to collect data (e.g., environmental data, personal data, biological data, chemical data, location data, identification data, audio data, image data) and/or to transmit the collected data to the mobile transceiver 110 via the antenna 139. The transceiver 130 can be, for example, a sensor, a meter, a monitor, and/or any other device capable of communicating with the mobile transceiver 110 over the wireless PAN 122. In some embodiments, the transceiver 130 is an implant and/or constructed from a biocompatible material such that the transceiver 130 can be implanted within a body of a patient.

In use, the mobile transceiver 110 operates similar to a smartphone (e.g., a BlackBerry® or iPhone®) and is capable of transmitting and receiving calls and/or data (e.g., email or Internet access) from other devices via the wireless network 120. The mobile transceiver 110 includes additional functionality that allows it to query, transmit data to and/or transmit power to the transceiver 130 when the transceiver 130 is located within range of the wireless PAN 122. In embodiments where the transceiver 130 is a glucose monitor implanted within a patient's body, the mobile transceiver 110 can transmit a data signal to the transceiver 130 via the wireless PAN 122, requesting that the transceiver 130 collect glucose data from the patient. Upon receiving the signal from the mobile transceiver 110, the transceiver 130 can initiate glucose data collection. The transceiver 130 can then transmit the collected glucose data to the mobile transceiver 110 via the wireless PAN 122. In some embodiments, the mobile transceiver 110 can analyze the collected glucose data it receives from the transceiver 130 via the wireless PAN 122 and/or display the collected glucose data, for example, on a display screen of the mobile transceiver 110 so that the user can view the collected glucose data.

In some embodiments, the mobile transceiver 110 can transmit a power signal to the transceiver 130 via the wireless PAN 122 in addition to or in lieu of the data signal. The transceiver 130 can be, for example, a passive device configured to power up and/or operate when it receives power from the mobile transceiver 110 via the wireless PAN 122. Once the transceiver 130 receives power from the mobile transceiver 110 via the wireless PAN 122, the transceiver 130 collects the glucose data and transmits the collected data to the mobile transceiver 110 in the manner described above. The transceiver 130 can then, for example, return to its inactive state or power down until it receives more power from the mobile transceiver 110. In some embodiments, the power received by the transceiver 130 from the mobile transceiver 110 is the only source of power for transceiver 130. In other embodiments, however, the transceiver 130 can receive or capture ambient energy from its surrounding environment via the antenna 139. The transceiver 130 can then convert the ambient energy into current and store the current until the transceiver 130 uses the power for operation (e.g., when the mobile transceiver 110 queries the transceiver 130 for glucose data or after a predetermined time period).

The patient can operate the mobile transceiver 110 and initiate the mobile transmitter's 110 communication with the transceiver 130. For example, the patient can press a button on the mobile transceiver 110 or activate a function of the mobile transceiver 110 that causes that mobile transceiver 110 to send a data signal and/or power signal to the transceiver 130 via the wireless PAN 122 to initiate data collection. In some embodiments, however, the mobile transceiver 110 automatically initiates communication with the transceiver 130. For example, the mobile transceiver 110 can be programmed to query the transceiver 130 for glucose data every 3 hours and/or to send power to the transceiver 130 every 3 hours for data collection.

In some embodiments, the transceiver 130 is programmed to operate solely with the mobile transceiver 110. The transceiver 130, for example, can be synchronized with, registered with, or operatively coupled to the mobile transceiver 110 so that the transceiver 130 and the mobile transceiver 110 communicate with each other using a specific protocol including protocols with security. The protocol can be, for example, a cellular protocol, WiFi®, Bluetooth®, near-field communication and/or the like.

In some embodiments, the mobile transceiver 110 can communicate with the wireless network 120 simultaneously with communication to the transceiver 130. Additionally, the mobile transceiver 110 can send power to the transceiver 130 at the same time as communicating data with the wireless network 120. The power sent to the transceiver 130 can be the same signal used to communicate data to the wireless network 120 or can be a different signal within the same or different frequency band.

In some embodiments, the transceiver 130 can communicate with the mobile transceiver 110 via the wireless network 120 and can receive operational power from RF power from the mobile transceiver 110 via the wireless PAN.

In some embodiments, the transceiver 130 can receive only operational power and/or data from the mobile transceiver 110 and may not communicate back to the mobile transceiver 110. Data obtained by the transceiver 130 as described herein can be presented (e.g. by display, by audio) and/or stored locally to the transceiver 130 and/or transmitted to another transceiver (not shown).

It should be noted that the transceiver as described herein can refer to a transmitter, receiver, or any combination.

Although FIG. 1 only shows one mobile transceiver 110 and one transceiver 130, multiple transceivers are possible. Examples of multiple transceivers for sending power and multiple transceivers for receiving power are described in U.S. Patent Application Publication 2008/0054729, entitled "RF Powered Specialty Lighting, Motion, Sound" and filed on Aug. 30, 2007; and U.S. Patent Application 60/841,819, entitled "RF Powered Specialty Lighting, Motion, Sound" and filed on Sep. 1, 2006; each of which is incorporated herein by reference.

Figure 2:
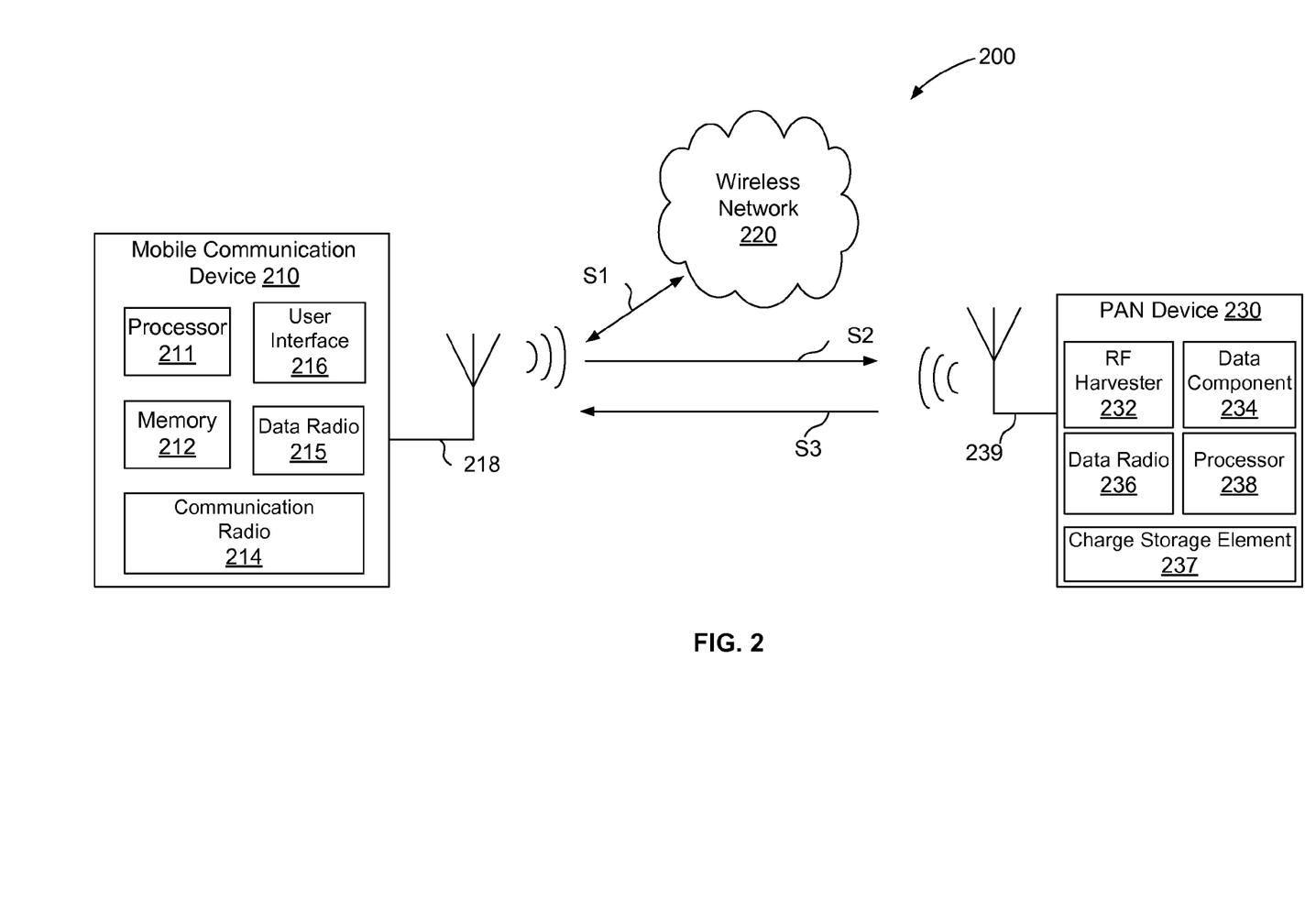
FIG. 2 is a schematic illustration of a wireless powering system having a mobile communication device and a PAN device, according to an embodiment.

FIG. 2 is a schematic illustration of a wireless powering system 200 for powering devices in a wireless personal area network (PAN). The system 200 includes a mobile communication device 210, a PAN device 230 and a wireless network 220. The mobile communication device 210 is configured to have some, if not all, of the functionality of a smartphone or other like device. For example, the mobile communication device 210 can communicate with other devices (e.g., other mobile communication devices) via the wireless network 220, including sending and receiving phone calls and/or data (e.g., emails, text messages, pictures, video). The mobile communication device 210 is also configured to communicate with the PAN device 230 when the PAN device 230 is located within a personal area network (not shown in FIG. 2) of the mobile communication device 210. The mobile communication device 210 can communicate with the PAN device 230, for example, via a protocol, such as a cellular protocol, WiFi®, Bluetooth®, near-field communication and/or the like in any appropriate frequency band (e.g. RF band, Cellular band, ISM band, Licensed band, Unlicensed band). The wireless network 220 can be any suitable wireless network, such as, for example, a wireless local area network (LAN), a wireless wide area network (WAN), a WiMAX, a cellular network, and/or the like.

The mobile communication device 210 includes a processor 211, a memory 212, a data radio 215, a communication radio 214, a user interface 216, and an antenna 218 (collectively, "components"). The memory 212 is configured to store data and/or software (e.g., computer programs) related to the general operation of the mobile communicate device 210. The memory 212 can also be configured to store data received from the PAN device 230 as well as information regarding the protocol used by the mobile communication device 210 to communicate with the PAN device 230. The memory 212 can be any of the memories discussed herein. The processor 211 can be configured to control the operation of the mobile communication device 210 and/or any one of the remaining components of the mobile communication device 210. Additionally, the processor 211 can be configured to execute the software stored within the memory 212. The processor 211 can be any of the processors discussed herein. The user interface 216 can be, for example, a display, a touch screen, or monitor (e.g., with speaker) configured to display data, images, video, multimedia, audio, etc. of the mobile communication device 210. In some embodiments, the user of the mobile communication device 210 can operate the mobile communication device 210 using the user interface 216. The data radio 215 is configured to communicate with the PAN device 230. The communication radio 214 is configured to communicate over the wireless network 220—e.g., for typical smartphone communications. In this manner, the mobile communication device 210 can communicate with the PAN device 230 in a separate band using a different radio than the band used for cellular operations. In some embodiments, however, the mobile communication device 210 communicates with the PAN device 230 using the same band and/or the same radio as that used for cellular operations.

The antenna 218 of the mobile communication device 210 is configured to receive the signals generated from the data radio 215 or the communication radio 214 and transmit those signals (S1 or S2, respectively) over the wireless network 220. For example, the antenna 218 can receive data signals representing emails or outbound phone calls from the communication radio 214 and transmit those signals (S1) over the wireless network 220. The antenna 218 can receive data signals (S1) transmitted over the wireless network 220 from other devices in the same manner. The antenna 218 can also send data signals and/or power signals (S2) to the PAN device 230 using the protocols discussed above.

The PAN device 230 includes a RF harvester 232, a data radio 236, a processor 238, a charge storage element 237, a data component 234, and an antenna 239 (collectively, "components"). The processor 238 can be configured to control the general operation of the PAN device 230 and/or any of the remaining components of the PAN device 230. Additionally, the processor 238 can be configured to execute any program stored within itself or stored within any other component of the PAN device 230 (e.g., in a memory of the PAN device 230). The processor 238 can be any of the processors discussed above. The data radio 236 is configured to communicate with the data radio 215 of the mobile communication device 210. More particularly, the data radio is configured to generate a data signal to be sent from the antenna 239 of the PAN device 230, and the data signal (S3) is sent to the mobile communication device 210 in the manner discussed above (e.g., separate or same bands). The data component 234 is configured to collect, sense or measure data from its surrounding environment. The data component 234 can then send that data to the data radio 236 for transmission to the mobile communication device 210. The data component 234 can be, for example, a sensor, a meter, a monitor and/or other device capable of collecting, sensing or measuring data from its surrounding environment.

The antenna 239 of the PAN device 230 is configured to transmit data to (S3) and receive data from (S2) the mobile communicate device 210 using the protocols discussed above. The antenna 239 is also configured to receive or collect ambient energy from its surrounding environment to use as power (e.g., excess RF energy produced by the mobile communicate device 210 during data transmission or RF energy from other sources). In some embodiments, the antenna 239 can receive power signals transmitted from the mobile communicate device 210 in addition to or in lieu of the ambient energy.

The RF harvester 232 is configured to convert the energy or power received by the antenna 239 into current (e.g., direct current). The RF harvester 232 can include, for example, an AC-to-DC converter and/or other electrical components configured to effectively convert energy or power into current. Examples of RF harvesters are described in U.S. Patent Application Publication 2007/0178857, entitled "Method and Apparatus for High Efficiency Rectification for Various Loads" and filed on Oct. 26, 2006; U.S. patent application Ser. No. 12/951,367 entitled "Method and Apparatus for High Efficiency Rectification for Various Loads" and filed on Nov. 22, 2010; and U.S. Patent Application 60/729,792, entitled "Method and Apparatus for High Efficiency Rectification for Various Loads" and filed on Oct. 24, 2005; each of which is incorporated herein by reference. Other examples of RF harvesters are also described in U.S. Patent Application Publication 2009/0067208, entitled "Method and Apparatus for Providing Power" and filed on Sep. 10, 2008; and U.S. Patent Application 60/993,216, entitled "Method and Apparatus for Providing Power" and filed on Sep. 11, 2007; each of which is incorporated herein by reference.

The charge storage element 237 is configured to store the converted current so that the current can be used to power the PAN device 230 at a future time. The charge storage element 237 can be, for example, a capacitor, a rechargeable battery and/or any other device capable of storing current for an extended period of time or recharging. In some embodiments, some of the current converted by the RF harvester 232 is not stored in the charge storage element but rather is used as operational power for the PAN device 230 almost immediately upon conversion. Examples of a charge storage element and the related modules for determining when to use converted power are described in U.S. patent application Ser. No. 12/125,532, entitled "Method, System and Apparatus for Harvesting Wirelessly Received Power" and filed on May 22, 2008; and U.S. Patent Application 60/931,481, entitled "Smart Receiver and Method" and filed on May 23, 2007; each of which is incorporated herein by reference.

As shown in FIG. 2, the mobile communication device 210 sends a data signal (S2) to the PAN device 230, for example, requesting data from the PAN device 230. In response to the data signal (S2), the PAN device 230 collects data via the data component 234. For example, in embodiments where the data component 234 is a glucose monitor (or meter), the glucose monitor would begin collecting data or transfer data collected at a previous time and stored in a memory (not shown) to the data radio 236 for transmission to the mobile communication device 210 in response to the data and/or power signal (S2) from the mobile communication device 210. The antenna 239 of the PAN device 230 transmits (S3) the collected data to the mobile communication device 210 in the manner discussed above. Upon receipt of the collected data (S3), the mobile communication device 210 can store the received data in the memory 212 for future use, analyze the received data via the processor 211, transmit the received data to the wireless network 220, and/or display the received data via the user interface 216 such that the user of the mobile communication device 210 can view or interact with the received data. The received data can be displayed or presented to the user of the mobile communication device 210 via graphic display or audible signal. The user of the mobile communication device 210 can interact with the received data via tactile interaction, voice commands, or data logging.

In some embodiments, the mobile communication device 210 does not initiate communication with the PAN device 230 as described above. Rather, the PAN device 230 is configured to automatically transmit data (S3) to the mobile communication device 210 on a scheduled basis or on a threshold of sufficient energy that is received and harvested from periodic power transmissions (S2) and/or received and harvested from communication signals from the mobile communication device 210 and/or the wireless network 220.

Figure 3:
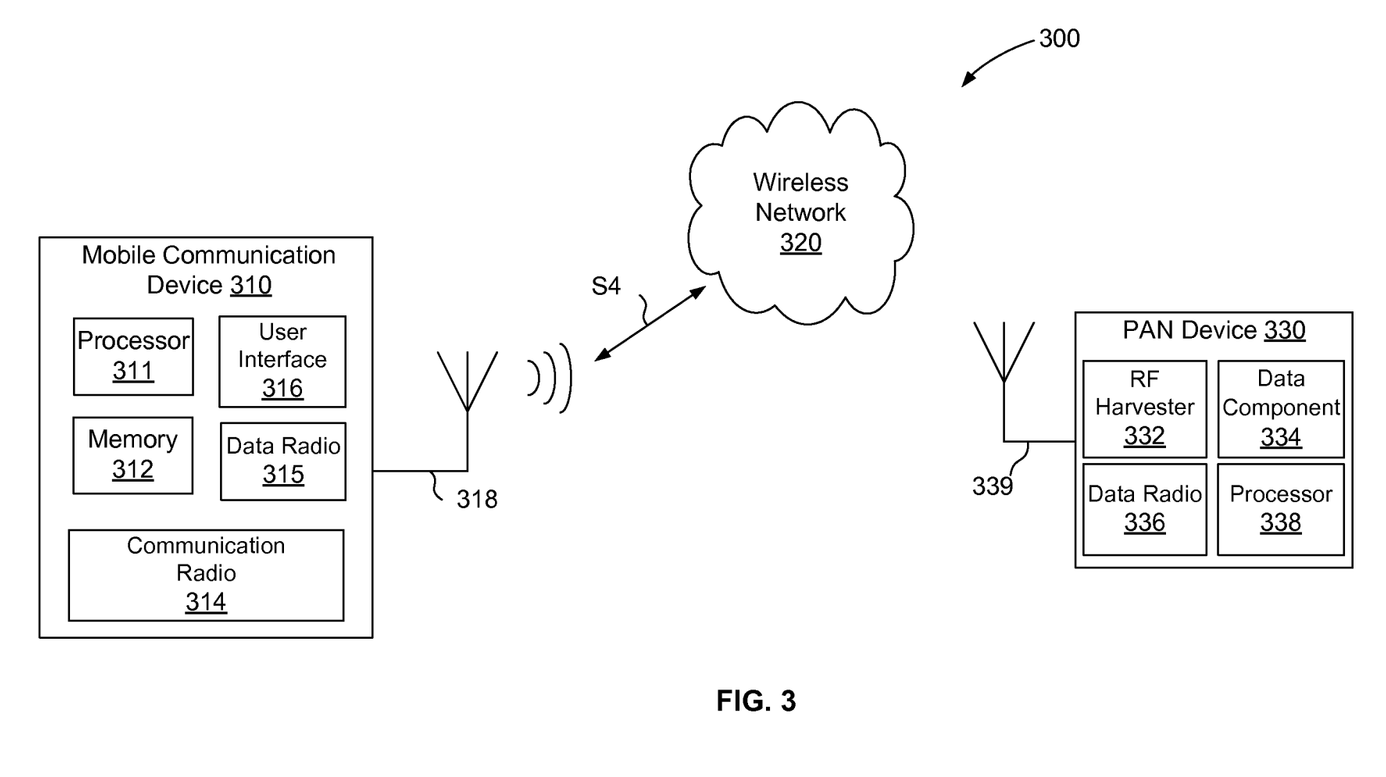
FIG. 3 is a schematic illustration of a wireless powering system having a mobile communication device operating in a first mode and a PAN device, according to an embodiment.
Figure 4:
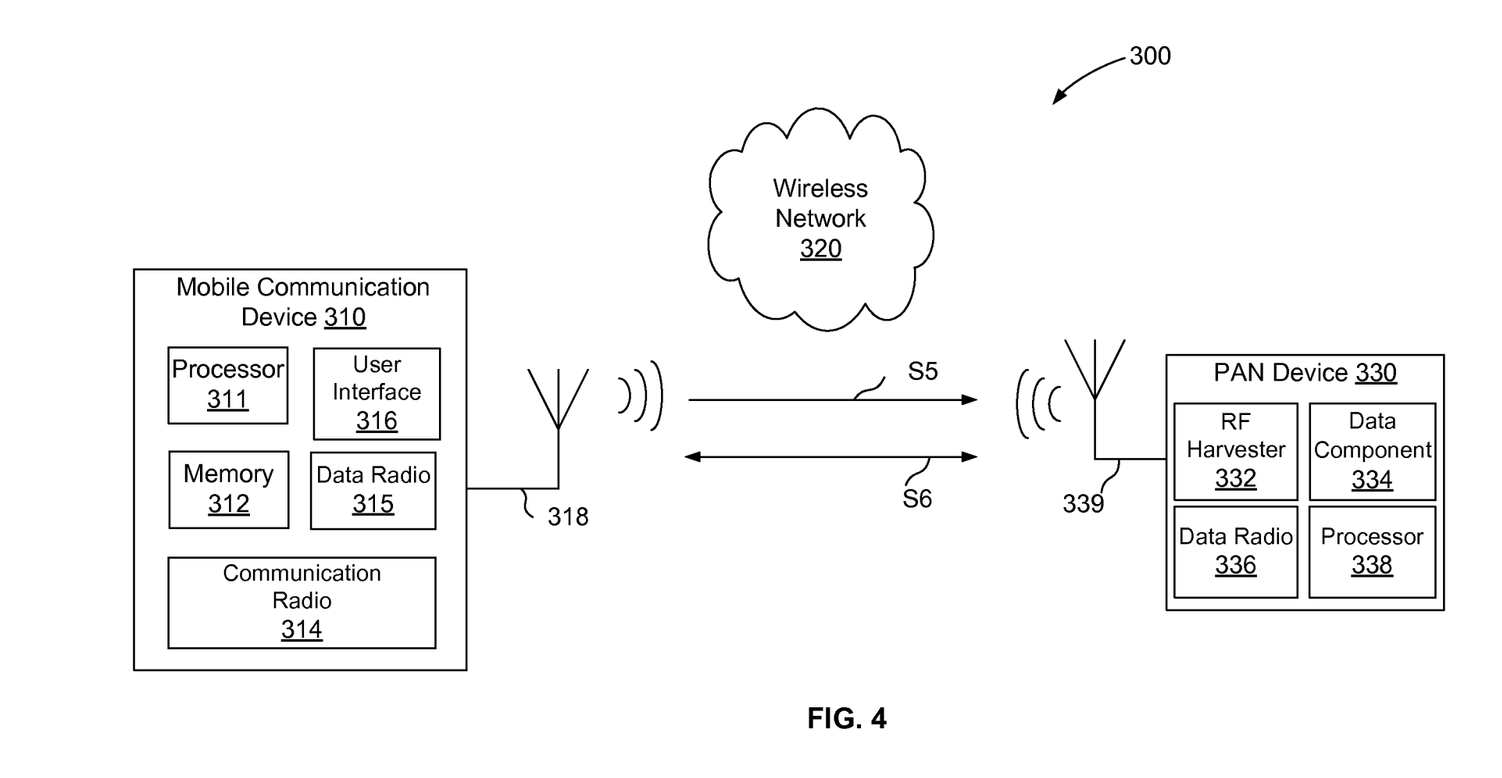
FIG. 4 is a schematic illustration of the wireless powering system shown in FIG. 3 where the mobile communication device is operating in a second mode, according to an embodiment.

FIGS. 3 and 4 are schematic illustrations of a wireless powering system 300 having a mobile communication device 310 operating in a first mode and a second mode, respectively. The system 300 includes the mobile communication device 310, a PAN device 330 and a wireless network 320. The mobile communication device 310 includes a processor 311, a memory 312, a data radio 315, a communication radio 314, a user interface 316, and an antenna 318 (collectively, "components"). The components of the mobile communication device 310 have substantially the same structure and function as the respective components of the mobile communication device 210 shown in FIG. 2 and, therefore, are not discussed in detail herein. The PAN device 330 includes a RF harvester 332, a data radio 336, a processor 338, a data component 334, and an antenna 339 (collectively, "components"). The components of the PAN device 330 have substantially the same structure and function as the respective components of the PAN device 230 shown in FIG. 2 and, therefore, are not discussed in detail herein.

When the mobile communication device 310 is in the first mode, the mobile communication device 310 operates in a normal smartphone manner to produce voice or data transmission over the wireless network 320. FIG. 3, for example, shows the mobile communication device 310 in the first mode transmitting a signal (S4) representing the voice or data via the antenna 318. When the mobile communication device 310 is in the second mode, the mobile communication device 310 is transmitting power (S5) to the PAN device 330, as shown in FIG. 4. Unlike the PAN device 230 shown in FIG. 2, the PAN device 330 of FIGS. 3 and 4 does not include a charge storage element for operation between powering signals (S5) and, therefore, uses energy from another source to operate. Here, the PAN device 330 receives power from the mobile communication device 310 when the mobile communication device 310 is operating in the second mode. In this manner, the PAN device 330 is operational when the mobile communication device 310 is operating in the second mode. In some embodiments, the antenna 339 of the PAN device 330 is configured to receive ambient energy as discussed above to power itself in addition to the power received from the mobile communication device 310. In some embodiments, the PAN device 330 includes a charge storage element.

In some embodiments, the mobile communications device 310 can operate in more than one mode. For example, while in a first mode, the communication device 310 can produce a communication signal (S4) to communicate to the wireless network 320 at a first power level, in a first frequency band, and/or using a first transmission protocol. While in a second mode, the communication device 31 can produce a communication and/or power signal (S5) at a second power level, in a second frequency band, and/or using a second transmission protocol. Note that the signal, S5, can be used for communicating from the mobile communication device 310 to the wireless network 320 at the same time as providing power to the PAN device 330. As an example, the mobile communication device 310 can increase the power of signal S4 used for normal communications to provide a sufficient power and/or data signal S5 to the PAN device 330.

In some embodiments, some of the smartphone functions accessible to the mobile communication device 310 during operation in the first mode are not accessible to the mobile communication device 310 during operation in the second mode. For example, the user of the mobile communication device 310 may not be able to send non-voice data when the mobile communication device 310 is operating in the second mode. In some embodiments, however, functions or features that were not accessible to the user when the mobile communication device 310 was operating in the first mode are accessible to the user when the mobile communication device 310 is operating in the second mode. For example, the processor 311 of the mobile communication device 310 can execute a software application that allows a user of the mobile communication device 310 to control the power and/or data transmission to the PAN device 330. In some embodiments, the user can enable power transmission to the PAN device 330 at a particular power level for a particular period of time via interaction with the software application. In this manner, the user can ensure that the PAN device 330 receives the appropriate amount of energy for operation.

In some embodiments, the software application executed by the processor 311 of the mobile communication device 310 can automatically adjust the power level, protocol, frequency band, or other parameter of the mobile communication device 310 to allow the mobile communication device 310 to communicate to the wireless network 320 while at the same time providing power (and data, if applicable) to the PAN device 330 when prompted by the user or configured to do so.

In some embodiments, the software application executed by the processor 311 of the mobile communication device 310 can limit the power level and/or duration of the power signals (S5) based on the communication function of the mobile communications device or the PAN or geographical location. For example, during voice data transmissions, the power level can be reduced when compared to other data transmissions (e.g. text messages, WiFi data, email data) due to close proximity of the mobile communication device 310 to the user. The mobile communication device 310 can include a sensor (not shown) used to determine or estimate the location of the mobile communication device 310 with respect to the user. For example, the mobile communication device 310 can include GPS hardware that determines the geographical location of the mobile communication device 310. Information representing the geographical location can be used, for example, by the processor or some other component of the mobile communication device 310, to select an unlicensed frequency band (or some other suitable frequency band) that is available at that location to transfer power and/or data to the PAN device 330. Examples of an unlicensed frequency band include industrial, scientific and medical (ISM) bands and radio-frequency identification (RFID) bands. In some embodiments, the GPS hardware is disposed within the mobile communication device 310 while, in other embodiments, the GPS hardware is located external from the mobile communication device 310 (e.g., externally attached). In some embodiments, the operation of the GPS hardware is manually triggered—e.g., the user of the mobile communication device 310 can press a button on the mobile communication device 310 that causes the GPS hardware to start collecting GPS data to determine the geographical location of the mobile communication device 310. In other embodiments, the operation of the GPS hardware is automatically triggered—e.g., the GPS hardware can be configured to automatically collect GPS data repeatedly, e.g., every 20 minutes (or at some other suitable time period, or set of time intervals).

For another example, it has been demonstrated that an iPhone® was able to power a wireless sensor including temperature, humidity, and light level sensors from the P2110-EVAL-01 development kit from Powercast Corporation. The wireless sensor was able to receive operational power from the iPhone® when within four feet. Power transmission from the iPhone® was initiated by the user by sending a text or email message in 2G mode. The wireless sensor harvested the GSM RF energy at ~825 MHz using the P2110 harvesting module from Powercast Corporation. The sensor sent data via 2.45 GHz to an access point connected to a computer. The computer was used to visualize the data transmission.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

In some embodiments, the mobile communication devices and the PAN devices can include or relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

Although various embodiments have been described as having particular features and/or combinations of components, other embodiments are possible having a combination of any features and/or components from any of the embodiments where appropriate.

What is claimed is:

1. An apparatus, comprising:
a transceiver configured to operate in a first mode and a second mode, the transceiver configured to transmit voice data and non-voice data over a first wireless network when the transceiver is in the first mode,
when the transceiver is in the second mode, the transceiver is configured to transmit operational power over a second wireless network to an electronic device secured to a user of the apparatus such that the electronic device collects data associated with the user using the operational power received from the transceiver, the transceiver configured to receive the data from the electronic device over the second wireless network when the transceiver is in the second mode, the second wireless network being different from the first wireless network.

2. The apparatus of claim 1, wherein the transceiver is configured to transmit a data signal to the electronic device over the second wireless network to prompt the electronic device to collect the data associated with the user when the transceiver is in the second mode.

3. The apparatus of claim 2, wherein the transceiver is configured to transmit the data signal separate from the operational power.

4. The apparatus of claim 1, wherein the transceiver is configured to transmit the operational power to the electronic device over the second wireless network when the transceiver and the electronic device are located within an operational range of the second wireless network.

5. The apparatus of claim 1, wherein the transceiver is electrically coupled to a display, the transceiver configured to transmit the data associated with the user to the display such that the data associated with the user is displayed on the display when the transceiver is in the second mode.

6. The apparatus of claim 1, wherein the transceiver is configured to transmit voice data but not transmit non-voice data over the first wireless network when the transmitter is in the second mode.

7. The apparatus of claim 1, wherein the electronic device is operational when the transceiver is in the second mode and not operational when the transceiver is in the first mode.

8. The apparatus of claim 1, wherein the electronic device is one of a sensor worn by the user, a sensor implanted within the user, a monitor worn by the user, or a monitor implanted within the user.

9. The apparatus of claim 1, wherein the first wireless network is a cellular network.

10. The apparatus of claim 1, wherein the second wireless network is a wireless personal area network.

11. The apparatus of claim 1, wherein the first mode is the primary mode of operation of the transceiver.

12. The apparatus of claim 1, wherein the operational power is pulsed radio frequency (RF) power.

13. The apparatus of claim 1, wherein the transceiver is a mobile transceiver.

14. A non-transitory processor-readable medium storing code representing instructions to cause a processor of a mobile communication device to perform a process, the code comprising code to:

transmit a signal representing voice data to a first electronic device over a wireless cellular network during a first operational mode;

transmit a power signal to a second electronic device over a wireless personal area network (PAN) during a second operational mode, the power signal configured to activate the second electronic device when the second electronic device receives the power signal such that the second electronic device is operable to collect data;

receive a signal representing the data from the second electronic device over the wireless PAN during the second operational mode; and send an output associated with the data received from the second electronic device to a display screen of the mobile communication device such that the output is displayed on the display screen.

15. The processor-readable medium of claim 14, further comprising code to:

after the power signal is transmitted, transmit a data signal to the second electronic device over the wireless PAN, the data signal configured to prompt the second electronic device to collect data when the second electronic device receives the data signal.

16. The processor-readable medium of claim 14, further comprising code to:

disable at least one feature of the mobile communication device during the second operational mode, the at least one feature being enabled during the first operational mode.

17. The processor-readable medium of claim 14, wherein the signal representing voice data is transmitted at a first power level, the power signal is transmitted at a second power level different from the first power level.

18. The processor-readable medium of claim 14, wherein the data collected at the second electronic device is at least one of environmental data, personal data, biological data, chemical data, location data, identification data, audio data, or image data.

19. A system, comprising:

a wireless electronic device configured to be secured to a body of a patient, the wireless electronic device configured to collect data associated with the patient when the wireless electronic device is activated; and a mobile communication device operable in a first mode and a second mode, the mobile communication device wirelessly transmits a voice data signal to a remote device over a first frequency band when the mobile communication device is operating in the first mode, when the mobile communication device is operating in the second mode, the mobile communication device wirelessly transmits a power signal to the wireless electronic device over a second frequency band different from the first frequency band to activate the wireless electronic device such that data associated with the patient is collected at the wireless electronic device.

20. The system of claim 19, wherein, when the mobile communication device is operating in the second mode, the mobile communication device transmits a query signal to the wireless electronic device over the second frequency band to prompt the wireless electronic device to collect data associated with the patient.

21. The system of claim 19, wherein, when the mobile communication device is operating in the second mode, the mobile communication device wirelessly receives the data collected at the wireless electronic device over the second frequency band and displays an output associated with the data on a display screen of the mobile communication device.

22. The system of claim 19, wherein the mobile communication device includes a radio component configured to generate the voice data signal wirelessly transmitted over the first frequency band and to generate the power signal wirelessly transmitted over the second frequency band.

23. The system of claim 19, wherein the wireless electronic device is a glucose monitor configured to collect glucose data when the glucose monitor is activated by the power signal transmitted from the mobile communication device over the second frequency band.

24. The system of claim 19, wherein the mobile communication device is configured to only communicate with the wireless electronic device over the second frequency band.

25. The system of claim 19, wherein the wireless electronic device is deactivated when the mobile communication device is operating in the first mode.

26. The system of claim 19, wherein the first frequency band is a licensed frequency band and the second frequency band is an unlicensed frequency band.

* * * * *